(12) United States Patent
Mitsumori

(10) Patent No.: US 6,716,160 B2
(45) Date of Patent: Apr. 6, 2004

(54) ENDOSCOPE

(75) Inventor: Naotake Mitsumori, Saitama (JP)

(73) Assignee: Fuji Photo Optical Co. Ltd., Saitama (JP)

( * ) Notice: Subject to any disclaimer, the term of this patent is extended or adjusted under 35 U.S.C. 154(b) by 0 days.

(21) Appl. No.: 10/072,982

(22) Filed: Feb. 12, 2002

(65) Prior Publication Data
US 2002/0115907 A1 Aug. 22, 2002

(30) Foreign Application Priority Data

Feb. 16, 2001 (JP) ........................... 2001-040645

(51) Int. Cl.$^7$ ................................. A61B 1/04
(52) U.S. Cl. ........................... 600/131; 600/133
(58) Field of Search ...................... 600/131, 128, 600/130, 133, 101

(56) References Cited

U.S. PATENT DOCUMENTS

| | | | | | |
|---|---|---|---|---|---|
| 4,552,129 A | * | 11/1985 | Utsugi et al. | ............... | 600/131 |
| 5,588,950 A | * | 12/1996 | Sano et al. | ............... | 600/178 |
| 5,752,964 A | * | 5/1998 | Mericle | ............... | 606/148 |
| 6,004,264 A | * | 12/1999 | Sano et al. | ............... | 600/178 |
| 6,010,656 A | * | 1/2000 | Nomura et al. | ............... | 264/255 |
| 6,384,128 B1 | * | 5/2002 | Wadahara et al. | ............ | 524/496 |
| 6,457,917 B1 | * | 10/2002 | Nomura et al. | ........... | 428/308.4 |
| 6,547,722 B1 | * | 4/2003 | Higuma et al. | ............. | 600/133 |
| 2003/0069571 A1 | * | 4/2003 | Treat et al. | ............... | 606/29 |

FOREIGN PATENT DOCUMENTS

JP          2-43484          9/1990

* cited by examiner

*Primary Examiner*—Beverly M. Flanagan
(74) *Attorney, Agent, or Firm*—Birch, Stewart, Kolasch & Birch, LLP

(57) ABSTRACT

The endoscope has a frame member for satisfying at a time, mechanical strength chemical resistance, size reduction, weight reduction, and workability by using carbon fiber reinforced thermoplastic resin as a frame member disposed inside the endoscope. The frame member of an at-hand operating part is formed by using carbon fiber reinforced thermoplastic resin. In the carbon fiber reinforced thermoplastic resin, substantially 20% to substantially 30% of carbon fiber is contained in a mixed material prepared by mixing crystalline resin and amorphous resin in a ratio of substantially 7:3 to substantially 8:2.

7 Claims, 8 Drawing Sheets

ENDOSCOPE

BACKGROUND OF THE INVENTION

1. Field of the Invention

The present invention relates to an endoscope and particularly concerns a frame member in an at-hand operating part, an insertion part, or a light guide connector of an endoscope.

2. Description of the Related Art

Conventionally, in endoscopes, an operating part to operate the endoscope is connected to the base of an insertion part, which is inserted into a subject. The operating part includes a curving operation mechanism, a suction valve, and an air/water supply valve and so on. Various tubes, an angle operating wire, codes, a light guide, and so on, which attach and support the above members and are provided through the insertion part, are connected to or inserted into the operating part. Further, a light guide soft part with flexibility is connected thereto, in which a light guide for introducing light from a light source disposed outside, a video signal code connected to a display and so on, and tubes for supplying and discharging air and water are inserted.

The operating part needs to support the curving operation mechanism and the like so as to positively operate them, and needs to have strength for connecting the insertion part. For example, as shown in FIGS. 8 to 10, an at-hand operating part disclosed in Japanese Patent Publication No. 2-43484 has an external component that is composed of a plastic case 1 and a rubber cover 2 and is electrically insulated. In the external component, a base plate 3 and a guide tube 4 are provided as frame members. A pulley having an angle operating wire wounded (not shown) is rotatably disposed on the base plate 3, and the angle operating wire and the contents of an endoscope are inserted into the guide tube 4 and are protected.

The base plate 3 and the guide tube 4 are connected to each other via connecting members 5 and are fixed by screws 6. The base plate 3 and the guide tube 4 allow the at-hand operating part to obtain mechanical strength.

Endoscopes need to be dipped into a chemical solution and/or to be subjected to gas sterilization after use for disinfection and sterilization. Gas sterilization is performed in an atmosphere of EOG (ethylene oxide gas) or hydrogen peroxide plasma gas. This sterilization is carried out by filling gas after reducing a pressure in a sterilizer. In general, since the endoscope entirely have an air-tight structure, in order to have equal pressures inside and outside the endoscope so as to prevent the endoscope from being damaged by a pressure difference between the inside and outside of the endoscope when a pressure is reduced, a vent is provided for connecting the inside and outside of the endoscope upon sterilization. Hence, when gas is filled, the gas enters the inside of the endoscope, and corrosion may occur if frame members made of aluminum are used.

Therefore, instead of aluminum prone to corrosion, corrosion-resistance stainless steel and titanium have been currently proposed as a frame member.

However, when stainless steel is adopted as a frame member, an at-hand operating part may be heavier and lower in operatability because stainless steel is large in specific gravity.

Meanwhile, when titanium is adopted as a frame member, in the case of a frame member having a complicated shape, working and assembling are necessary for each component having a simple shape because titanium is poor in workability and a worked shape is limited.

SUMMARY OF THE INVENTION

Against the above backdrop, a frame member with satisfactory mechanical strength, chemical resistance, size reduction, weight reduction, and workability has been desired.

The present invention has been developed in view of the above-mentioned circumstances and has its object to provide an endoscope which has a frame member being satisfactory in all of mechanical strength, chemical resistance, size reduction, weight reduction, and workability.

In order to attain the above object, the present invention is directed to an endoscope, comprising a frame member formed by using carbon fiber reinforced thermoplastic resin.

According to the present invention, since carbon fiber reinforced thermoplastic resin is used as a material of the frame member, it is possible to obtain sufficient mechanical strength and reduced weight as compared with metal. Further, carbon fiber reinforced thermoplastic resin has sufficient chemical resistance and can prevent corrosion of the frame member during disinfection and sterilization. Moreover, carbon fiber reinforced thermoplastic resin can be molded like other resins. Thus, even a complicated shape can be integrally formed.

Preferably, the frame member is a plate member provided in an endoscope at-hand operating part. Hence, the at-hand operating part can be lighter in weight.

Preferably, a tube member is connected to the plate member, and the tube member and the plate member are integrally formed. Hence, screws and the like are not necessary for connecting the tube member and the plate member. Therefore, by effectively using a space where screws and the like used to exist, the at-hand operating part can be smaller in size.

Preferably, the carbon fiber reinforced thermoplastic resin is prepared by mixing carbon fiber into a material selected from a group consisting of nylon-66, ABS, PC, PBT, denatured PPE, PPS, PET, and POM. Selection can be optionally made according to the shape and use.

Preferably, the carbon fiber reinforced thermoplastic resin contains substantially 20% to substantially 30% of carbon fiber. Hence, it is possible to achieve mechanical strength substantially equal to that of aluminum.

Preferably, the carbon fiber reinforced thermoplastic resin is a mixed material prepared by mixing crystalline material and amorphous resin; and the mixed material contains substantially 70% to substantially 80% of the crystalline resin. Hence, it is possible to improve workability such as size stability while maintaining excellent chemical resistance and mechanical strength that are advantages of crystalline resin.

BRIEF DESCRIPTION OF THE DRAWINGS

The nature of this invention, as well as other objects and advantages thereof, will be explained in the following with reference to the accompanying drawings, in which like reference characters designate the same or similar parts throughout the figures and wherein.

DETAILED DESCRIPTION OF THE PREFERRED EMBODIMENTS

Hereunder a preferred embodiment will be described for an endoscope of the present invention in accordance with the accompanied drawings.

Figure 1:
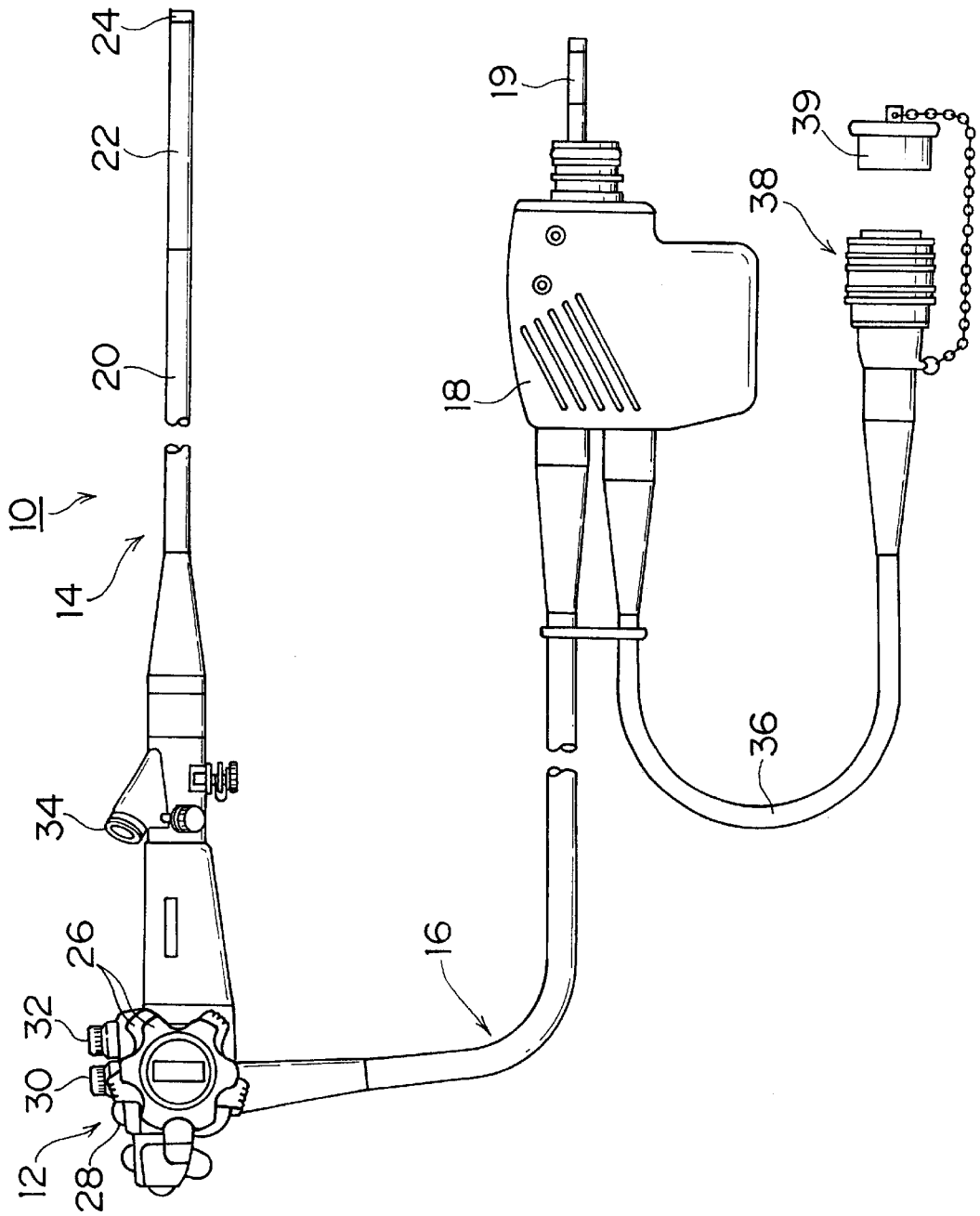
FIG. 1 is a structural diagram entirely showing an endoscope of the present invention.

An endoscope 10 of FIG. 1 comprises an at-hand operating part 12 and an insertion part 14 connected to the at-hand operating part 12. The insertion part 14 is composed of an insertion part side soft part 20, a curving part 22, and a distal end assembly 24. The curving section 22 is remotely curved by rotating a pair of curving knobs 26, which are provided on the at-hand operating part 12, and the distal end assembly 24 is pointed to a desired direction.

A forceps inserting opening 34 for inserting a treatment tool such as a forceps is provided on the at-hand operating part 12, and a shutter button 28, a suction button 30, and an air/water supply button 32 are provided in parallel on the at-hand operating part 12. Further, an LG (light guide) connector 18 is connected to the at-hand operating part 12 via an LG soft part 16. The LG connector 18 includes a light guide rod 19 connected to a light source device (not shown), and an electrical connector 38 is connected to the LG connector 18 via an electrical cable 36. Here, reference numeral 39 of FIG. 1 denotes a watertight cap of the electrical connector 38.

Figure 2:
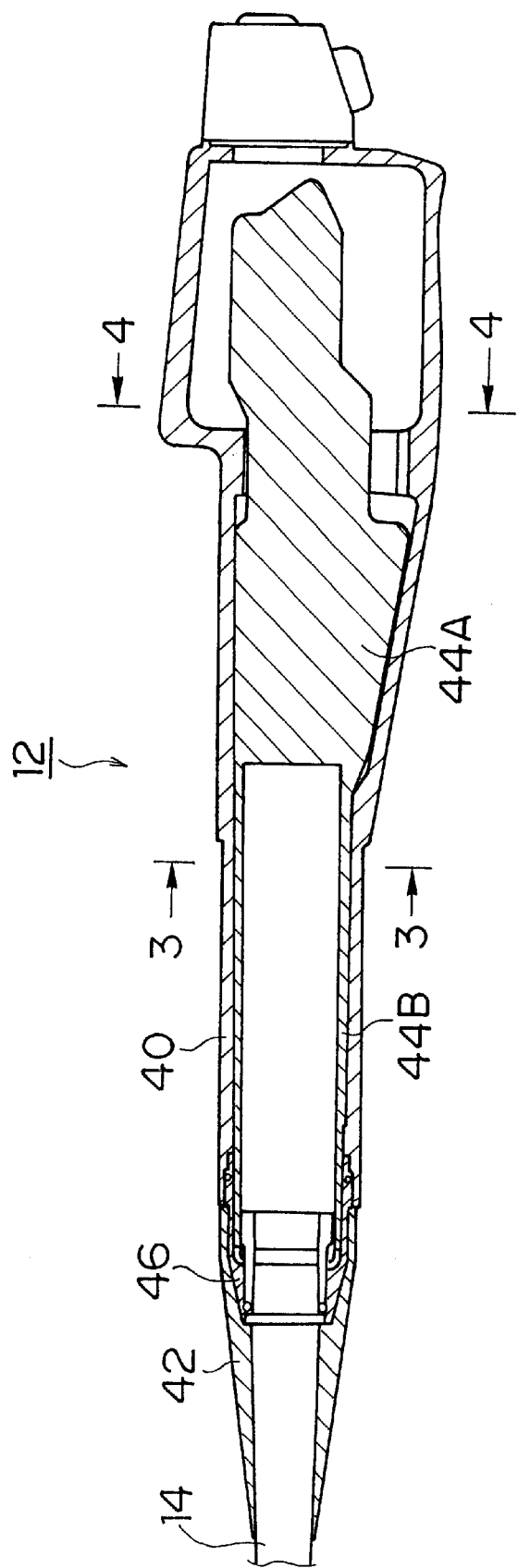
FIG. 2 is a schematic diagram showing the configuration of an at-hand operating part.

FIG. 2 is a schematic diagram showing the configuration of the at-hand operating part 12.

As shown in FIG. 2, for example, the at-hand operating part 12 has an external component composed of a case 40, which is made of plastic such as denatured PPE, and a cover 42 made of rubber. Thus, the at-hand operating part is electrically insulated.

A frame member 44 is provided in the at-hand operating part 12. The frame member 44 includes a base plate (equivalent to a plate member) 44A and a guide tube (equivalent to a tube member) 44B. The base plate 44A and the guide tube 44B are integrally formed.

Figure 3:
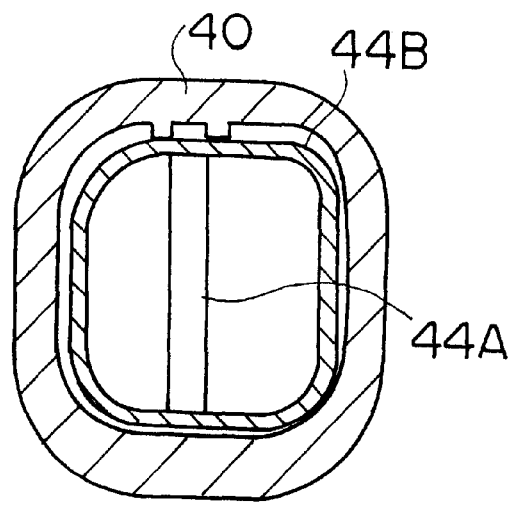
FIG. 3 is a sectional view showing the at-hand operating part taken along line 3—3 of FIG. 2.

The insertion part 14 is connected to the end of the guide tube 44B via a connecting tube 46. Moreover, as shown in FIG. 3, the guide tube 44B is formed in accordance with the shape of the case 40. Namely, like the internal shape of the case 40, the guide tube 44B is formed into a tube substantially rectangular in cross section.

Figure 4:
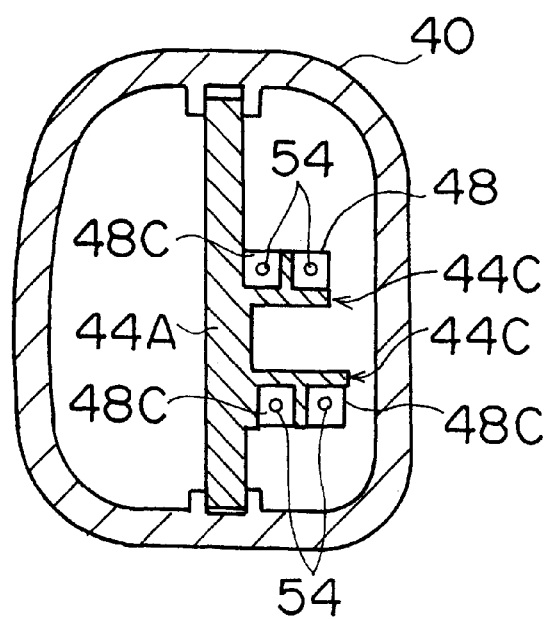
FIG. 4 is a sectional view showing the at-hand operating part taken along line 4—4 of FIG. 2.
Figure 5:
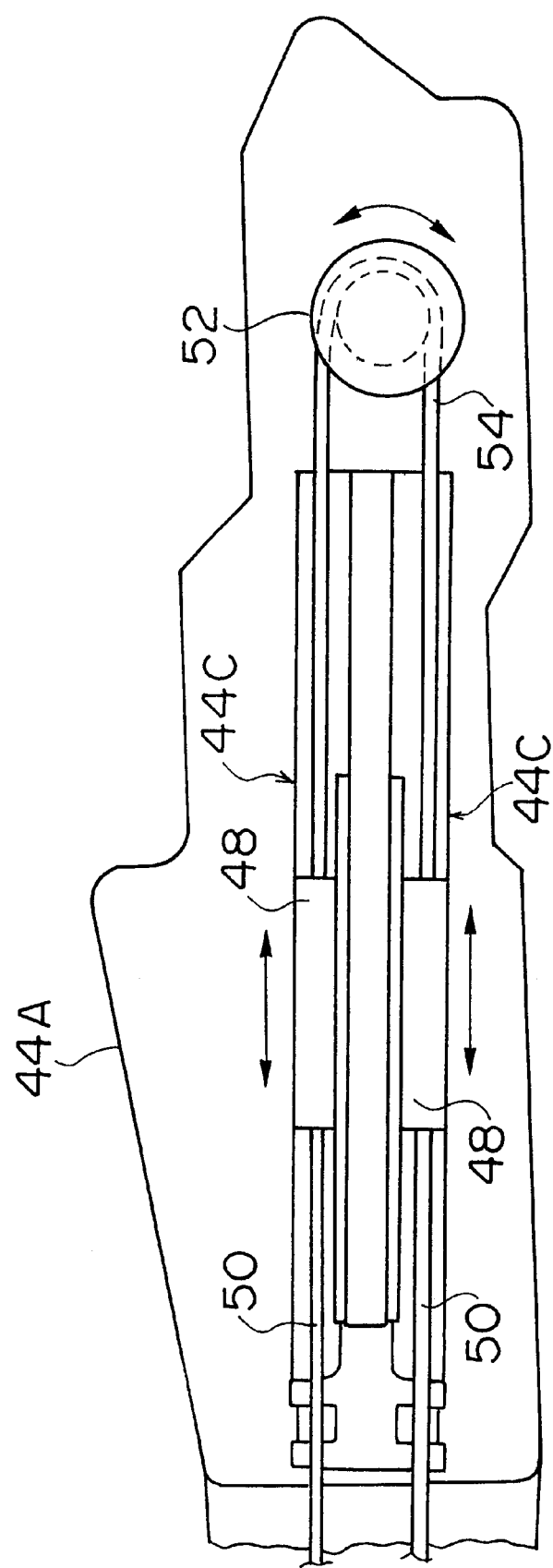
FIG. 5 is a plan view showing a base plate of a frame member.

As shown in FIGS. 4 and 5, protruding guides 44C are formed on the base plate 44A. Each of the guides 44C has rails formed on two stages, and connection pieces 48 are supported on the rails so as to slide freely. Operation wires 50 and wires 54 are connected to the connection pieces 48. The operation wires 50 are inserted through the insertion part 14 (see FIG. 1) and are connected to the curving part 22. Moreover, the wires 54 are looped over a pulley 52 and are connected to the connection pieces 48 supported by the other guide 44C. The pulley 52 is rotated by the curving knobs 26 (see FIG. 1). When the pulley 52 is rotated, the connection pieces 48 slide to push and pull the operation wires 50. And then, the curving part 22 of FIG. 1 is curved vertically or horizontally.

As a material of the frame member 44, carbon fiber reinforced thermoplastic resin is used, which is reinforced by mixing carbon fiber with resin material. As the resin material mixed with carbon fiber, it is possible to adopt at least a material selected from a group consisting of nylon-66, PBT (polybutylene terephthalate), PPS (polyphenylene sulfide), PET (polyethylene terephthalate), POM (polyoxymethylene polyacetals), ABS (acrylonitrile butadiene styrene resin), PC (polycarbonate), and denatured PPE (polyphenylene ether). A mixed material made by mixing a plurality of materials is also applicable. When a mixed material is used, it is preferable to mix crystalline resin (nylon-66, PBT, PPS, PET, POM) and amorphous resin (ABS, PC, PPE) in a 7:3 to 8:2 ratio. Here, crystalline resin is resin in which some molecules constituting a substance are gathered in a regular manner. The crystalline resin has strong molecular binding, thereby achieving high chemical resistance and mechanical strength such as hardness. Further, amorphous resin is resin in which molecules cannot be gathered in a regular manner. When using the amorphous resin, so-called recess is not likely to occur when a mold is formed, and size stability can be obtained with ease. With resin made by mixing crystalline resin and amorphous resin in the above ratio, it is possible to achieve size stability that is a characteristic of amorphous resin, while maintaining high chemical resistance and mechanical strength that are characteristics of crystalline resin.

As a ratio of contained carbon fiber, substantially 20% to substantially 30% is preferable. Carbon fiber reinforced thermoplastic resin made by containing carbon fiber in the above ratio is substantially half in specific gravity as compared with aluminum while being substantially equal to aluminum in mechanical strength.

As a preferable example of carbon fiber reinforced thermoplastic resin used for the frame member 44, it is possible to adopt resin in which PBT and PC are mixed in a 7:3 to 8:2 ratio and the mixed material contains substantially 20% to substantially 30% of carbon fiber. Besides, PET may be mixed instead of PC. Among crystalline resins, PET is relatively high in size stability, thereby improving size stability of the frame member 44.

The following will discuss the effects of the endoscope 10 configured thus.

Carbon fiber reinforced thermoplastic resin containing substantially 20% to substantially 30% of carbon fiber is substantially half in specific gravity as compared with aluminum while being substantially equal to aluminum in mechanical strength. Thus, the resin is extremely light in weight. Therefore, it is possible to obtain sufficient mechanical strength for the frame member 44 and to reduce the weight of the at-hand operating part 12.

Moreover, since crystalline resin and amorphous resin are mixed in a substantially 7:3 to substantially 8:2 ratio, it is possible to obtain high chemical resistance and mechanical strength and to further obtain excellent size stability for the frame member 44.

Figure 8:
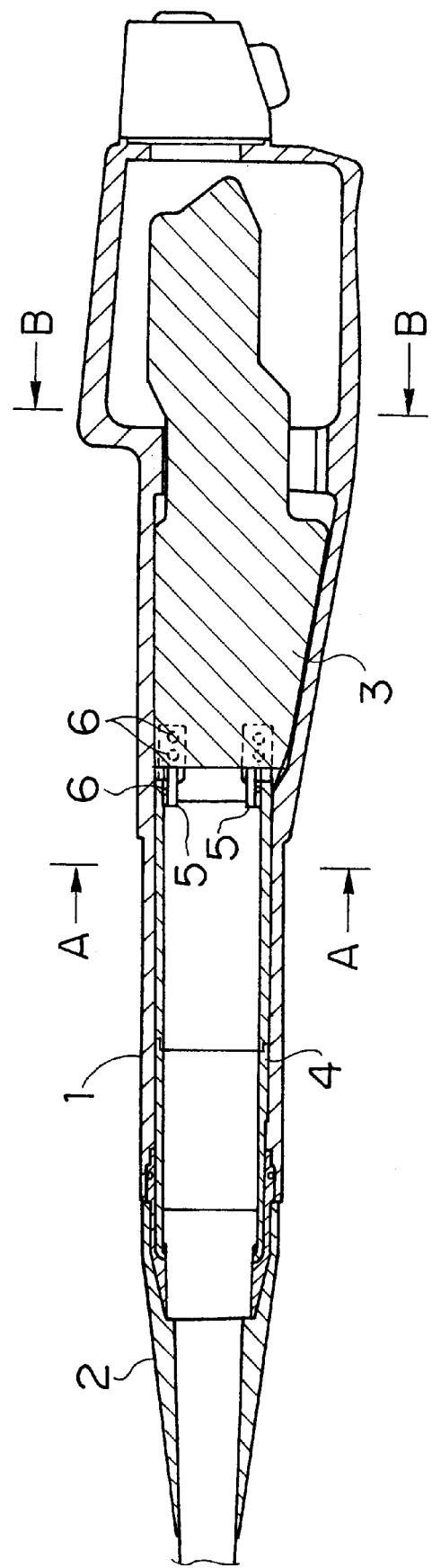
FIG. 8 is a schematic diagram showing the configuration of a conventional at-hand operating part.

Besides, carbon fiber reinforced thermoplastic resin can be molded like other plastics, and complicated shapes can be integrally formed. Hence, the base plate 3 and the guide tube 4 of FIG. 8 can be integrally formed as shown in FIG. 2. Therefore, it is not necessary to connect the base plate 3 and the guide tube 4 via the connecting tool 5 and the like, thereby improving assembling efficiency of the at-hand operating part 12. Additionally, since the connecting tool 5 and the screws 6 can be omitted, the at-hand operating part 12 can be smaller in size. Furthermore, it is possible to prevent damage on the contents because the contents are not caught on the screws 6.

Figure 9:
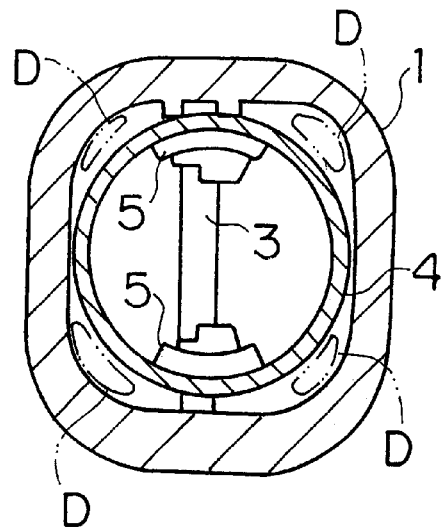
FIG. 9 is a sectional view showing the at-hand operating part taken along line A—A of FIG. 8.

Moreover, since the frame member 44 can be molded, as shown in FIG. 3, the section of the guide tube 44B can be formed into a rectangular according to the section of the case 40. Therefore, as shown in FIG. 9, as compared with the guide tube 4 formed into a cylinder, it is possible to eliminate a space D between the guide tube 4 and the case 1, thereby reducing the size of the at-hand operating part 12.

Figure 10:
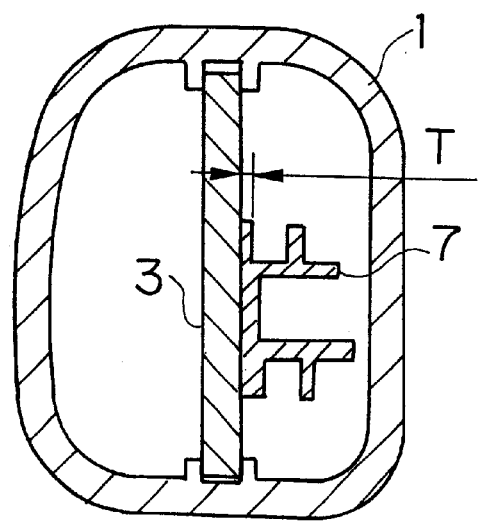
FIG. 10 is a sectional view showing the at-hand operating part taken along line B—B of FIG. 8.

Further, as shown in FIG. 4, the frame member 44 has the base plate 44A and the guides 44C that are formed integrally. Thus, as shown in FIG. 10, as compared with the base plate 3 and the guide 7 formed separately, a thickness T for attaching the guide 7 is not necessary. Therefore, the at-hand operating part 12 can be smaller in size.

Besides, the above-mentioned carbon fiber reinforced thermoplastic resin is applicable for a member disposed in the endoscope 10. With the carbon fiber reinforced thermoplastic resin, it is possible to obtain excellent chemical resistance and mechanical strength and to further achieve weight reduction, size reduction, and higher workability.

Figure 6:
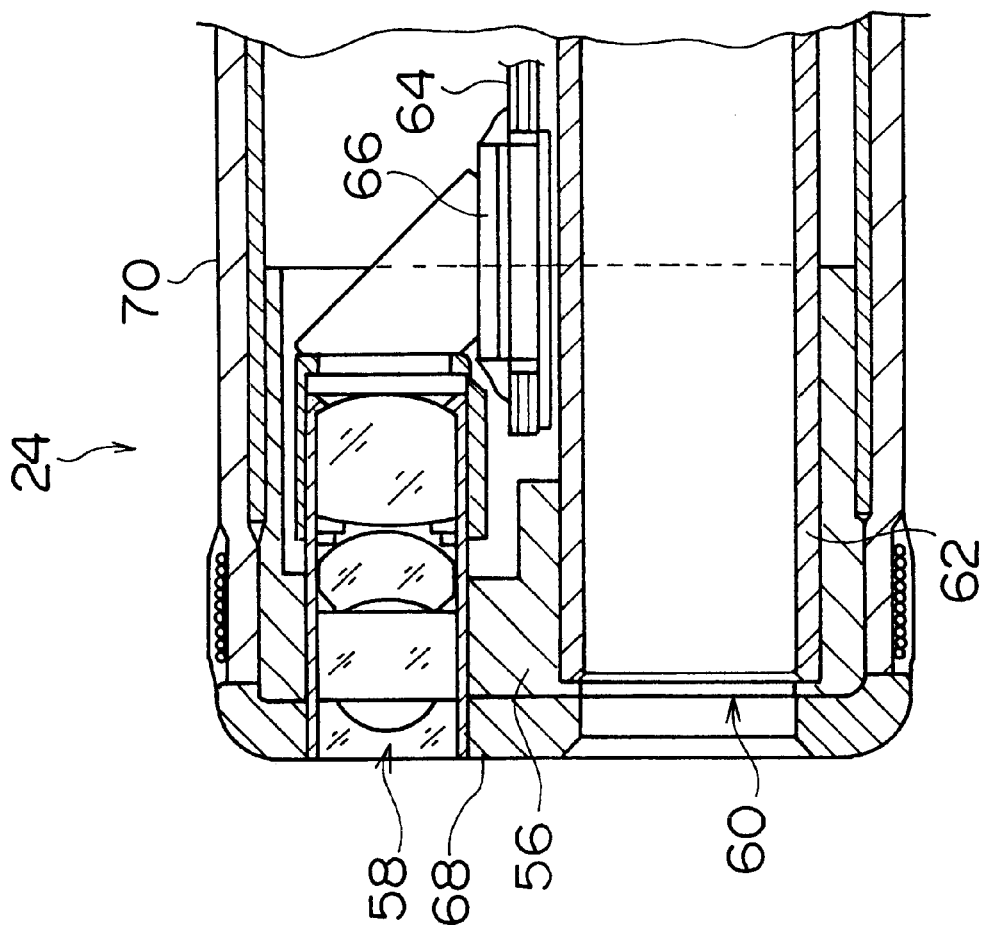
FIG. 6 is a schematic diagram showing the configuration of a distal end assembly.

For example, in the distal end assembly 24 of FIG. 6, a distal end body 56 serving as a frame member is formed using carbon fiber reinforced thermoplastic resin. The distal end body 56 is formed into a cylinder, and an objective optical system 58, a forceps opening 60, and the like are provided on the distal end body 56. The forceps opening 60 is connected to the forceps inserting opening 34 (see FIG. 1) via a forceps pipe 62 and a forceps tube (not shown) connected to the forceps pipe 62. Further, a CCD (solid-state image pickup element) 66 supported by a substrate 64 is provided at the rear of the objective optical system 58, and an observation image captured from the objective optical system 58 is formed on a light-receiving surface of the CCD 66.

A plastic cap 68 is attached to the end face of the distal end body 56. Further, the outer peripheral surface of the distal end body 56 is covered with an insulative covering tube 70. Thus, the outer surface of the distal end assembly 24 is insulated.

In the distal end assembly 24 configured thus, carbon fiber reinforced thermoplastic resin is used as a material of the distal end body 56. Hence, it is possible to sufficiently obtain mechanical strength of the distal end body 56 and reduce the weight of the distal end body 56. Therefore, since the distal end assembly 24 is light in weight, curving operability of the curving part 22 is improved when the curving knobs 26 of FIG. 1 are rotated.

Further, since the chemical resistance of the distal end body 56 is improved, when the distal end assembly 24 is subjected to chemical wash and gas sterilization, corrosion of the distal end body 56 can be prevented. Moreover, even when the distal end body 56 has a complicated shape, it can be integrally formed by molding.

Figure 7:
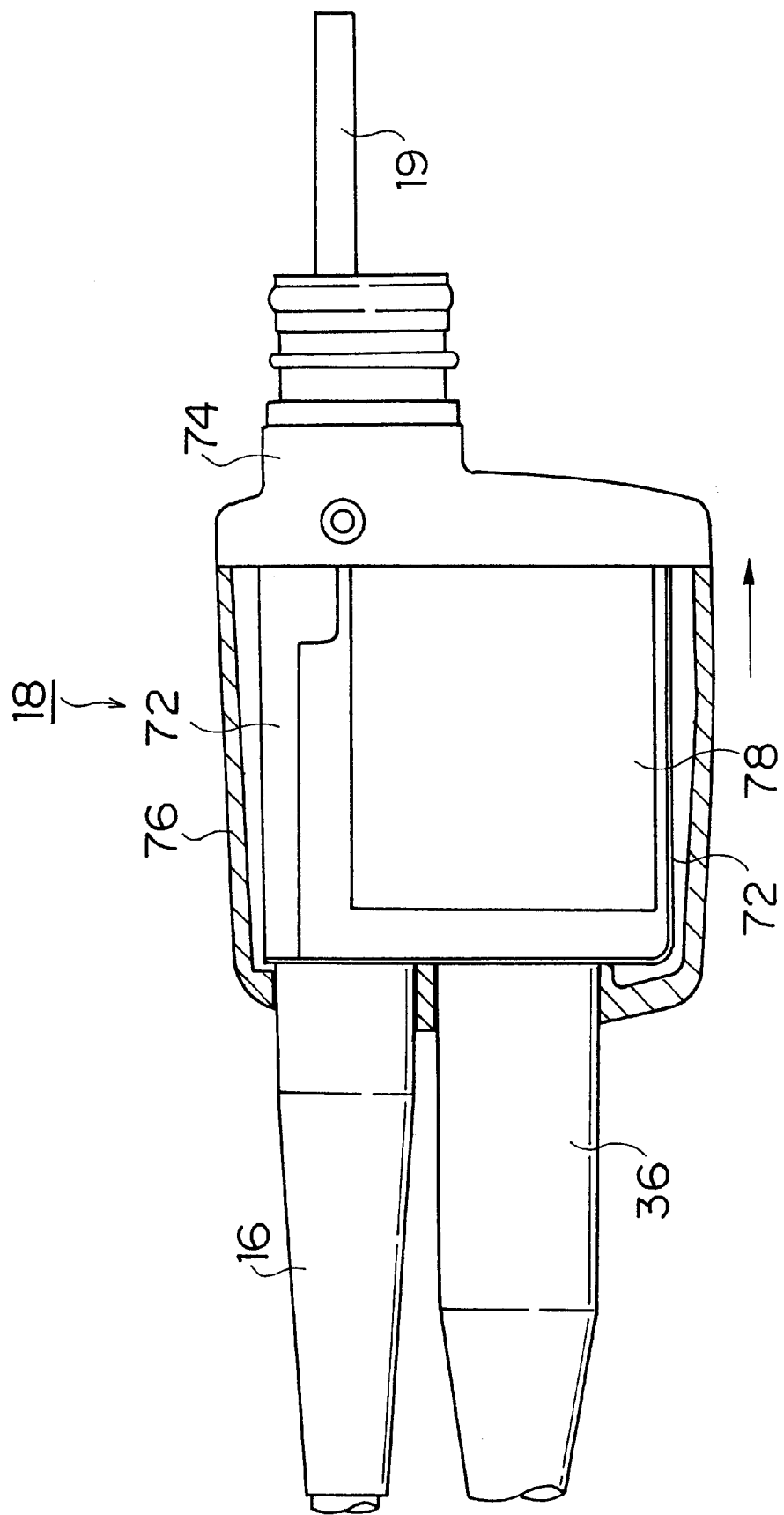
FIG. 7 is a schematic diagram showing the configuration of an LG connector.

Meanwhile, in the LG connector 18 of FIG. 7, a frame 72 serving as a frame member is formed by using carbon fiber reinforced thermoplastic resin. The frame 72 is attached to a base 74 having a light guide rod 19. The frame 72 is housed into the connector case 76 and the base 74 by sliding the connector case 76 in a direction of arrow and placing it onto the base 74. The base 74 and the connector case 76 are made of insulating plastic. The LG cable 16 and an electrical cable 36 are inserted into the connector case 76 and are fixed on the frame 72. The frame 72 has a substrate 78 therein.

In the LG connector 18 configured thus, carbon fiber reinforced thermoplastic resin is used as a material of the frame 72. Hence, it is possible to sufficiently obtain mechanical strength of the frame 72 and reduce the weight of the LG connector 18. Further, even when the frame 72 has a complicated shape, it can be integrally formed by molding. Therefore, as compared with the case where the frame 72 is formed by a plurality of members, connecting components such as screws are not necessary. Thus, the LG connector 18 can be smaller in size.

Additionally, since carbon fiber reinforced thermoplastic resin has conductivity, it cannot be used for a member (e.g., the case 40) constituting the outer surface of the endoscope 10. Hence, it is also possible to adopt resin in which no carbon fiber is contained and crystalline resin and amorphous resin are mixed in a ratio of substantially 7:3 to substantially 8:2. Therefore, it is possible to cover the outer surface of the endoscope with a material with excellent chemical resistance, mechanical strength, size stability, and an insulating characteristic.

As described above, according to the endoscope of the present invention, since carbon fiber reinforced thermoplastic resin is used as a material of the frame member, it is possible to achieve weight and size reduction while obtaining sufficient mechanical strength, and to achieve high chemical resistance.

It should be understood, however, that there is no intention to limit the invention to the specific forms disclosed, but on the contrary, the invention is to cover all modifications, alternate constructions and equivalents falling within the spirit and scope of the invention as expressed in the appended claims.

What is claimed is:

1. An endoscope, comprising:
   a frame member formed with carbon fiber reinforced thermoplastic resin, wherein the carbon fiber reinforced thermoplastic resin is a mixed material prepared with crystalline material and amorphous resin, the carbon fiber reinforced thermoplastic resin containing substantially 20% to substantially 30% of carbon fiber and substantially 70% to substantially 80% of the crystalline material; and
   a tube member integrally formed with and connected to the frame member, said tube member being formed with a rectangular-shaped cross section.

2. The endoscope according to claim 1, wherein the frame member is a plate member provided in an endoscope at-hand operating part.

3. The endoscope according to claim 1, wherein the carbon fiber reinforced thermoplastic resin is prepared by mixing carbon fiber into a material selected from a group consisting of nylon-66, ABS, PC, PBT, denatured PPE, PPS, PET, and POM.

4. The endoscope according to claim 1, further comprising a case enclosing the tube member and the frame member, said case having a rectangular-shaped internal surface.

5. The endoscope according to claim 4, wherein the rectangular shaped cross section of the tube member corresponds to the rectangular shaped inner surface of the case.

6. The endoscope according to claim 5, wherein the frame member and the tube member are connected without a connecting tool.

7. The endoscope according to claim 5, wherein the frame member and the tube member are connected without any screws.

* * * * *